United States Patent
Salo et al.

(10) Patent No.: US 8,295,928 B2
(45) Date of Patent: Oct. 23, 2012

(54) PRE-EXCITATION PACING FOR TREATMENT OF HYPERTENSION

(75) Inventors: Rodney W. Salo, Fridley, MN (US); Robert Shipley, Austin, TX (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 0 days.

(21) Appl. No.: 13/279,503

(22) Filed: Oct. 24, 2011

(65) Prior Publication Data

US 2012/0041505 A1 Feb. 16, 2012

Related U.S. Application Data

(62) Division of application No. 11/557,202, filed on Nov. 7, 2006, now Pat. No. 8,046,070.

(51) Int. Cl.
*A61N 1/365* (2006.01)
(52) U.S. Cl. .......................................................... 607/23
(58) Field of Classification Search ...................... 607/23
See application file for complete search history.

(56) References Cited

U.S. PATENT DOCUMENTS

| | | | |
|---|---|---|---|
| 4,566,456 A | 1/1986 | Koning et al. | |
| 5,076,280 A | 12/1991 | Moriuchi et al. | |
| 5,534,016 A | 7/1996 | Boute | |
| 5,891,176 A | 4/1999 | Bornzin | |
| 6,371,922 B1 | 4/2002 | Baumann et al. | |
| 6,580,946 B2 | 6/2003 | Struble | |
| 7,103,410 B2 * | 9/2006 | Kramer et al. | 607/9 |
| 7,245,970 B2 * | 7/2007 | Zhu et al. | 607/28 |
| 7,366,567 B2 | 4/2008 | Zhu et al. | |
| 2002/0087089 A1 | 7/2002 | Ben-Haim | |
| 2004/0147966 A1 | 7/2004 | Ding et al. | |
| 2005/0149128 A1 | 7/2005 | Heil, Jr. et al. | |
| 2005/0165454 A1 | 7/2005 | Chinchoy | |
| 2005/0267542 A1 | 12/2005 | David et al. | |
| 2006/0217772 A1 | 9/2006 | Libbus et al. | |
| 2007/0255346 A1 | 11/2007 | Rondoni et al. | |
| 2008/0109043 A1 | 5/2008 | Salo et al. | |

FOREIGN PATENT DOCUMENTS

| | | |
|---|---|---|
| WO | WO-0102049 A2 | 1/2001 |
| WO | WO-02087694 A1 | 11/2002 |
| WO | WO-2005028029 A2 | 3/2005 |
| WO | WO-2006008535 A1 | 1/2006 |
| WO | WO-2006101749 A1 | 9/2006 |
| WO | WO-2008057631 A1 | 5/2008 |

OTHER PUBLICATIONS

"U.S. Appl. No. 11/557,202 Non-Final Office Action mailed Sep. 16, 2010", 11 pgs.
"U.S. Appl. No. 11/557,202, Final Office Action mailed Mar. 17, 2011", 12 pgs.

(Continued)

*Primary Examiner* — Carl H Layno
*Assistant Examiner* — Jeremiah Kimball
(74) *Attorney, Agent, or Firm* — Schwegman Lundberg & Woessner, P.A.

(57) ABSTRACT

Described herein are methods and apparatus for treating hypertension with electrical pre-excitation pacing therapy. Electrical pre-excitation of a hypertrophic region advances the timing of the regional contraction and reduces its contribution to the overall contraction. Such pre-excitation pacing therapy may be beneficial to hypertensive patients with an abnormal distribution of ventricular wall stress/strain.

20 Claims, 5 Drawing Sheets

OTHER PUBLICATIONS

"U.S. Appl. No. 11/557,202, Final Office Action mailed Apr. 30, 2010", 11 pgs.

"U.S. Appl. No. 11/557,202, Non Final Office Action mailed Oct. 6, 2009", 11 pgs.

"U.S. Appl. No. 11/557,202, Notice of Allowance mailed Jun. 29, 2011", 7 pgs.

"U.S. Appl. No. 11/557,202, Response filed Jun. 17, 2011 to Final Office Action mailed Mar. 17, 2011", 6 pgs.

"U.S. Appl. No. 11/557,202, Response filed Aug. 13, 2009 to Restriction Requirement mailed Jul. 13, 2009", 6 pgs.

"U.S. Appl. No. 11/557,202, Response filed Jan. 6, 2010 to Non Final Office Action mailed Oct. 6, 2009", 7 pgs.

"U.S. Appl. No. 11/557,202, Response filed Dec. 16, 2010 to Non Final Office Action mailed Sep. 16, 2010", 8 pgs.

"U.S. Appl. No. 11/557,202, Response filed Aug. 30, 2010 to Final Office Action mailed Apr. 30, 2010", 7 pgs.

"U.S. Appl. No. 11/557,202, Restriction Requirement mailed Jul. 13, 2009", 8 pgs.

"Australian Application Serial No. 2007317752, Examiner Report mailed Jan. 20, 2011", 3 pgs.

"PCT Application Serial No. PCT/US2007/071852, International Search Report mailed Nov. 22, 2007", 5 pgs.

"PCT Application Serial No. PCT/US2007/071852, Wrriten Opinion mailed Nov. 22, 2207".

Lakatta, E. G., "Cardiovascular regulatory mechanisms in advanced age", Physiol Rev., 73(2), (Apr. 1993), 413-467.

Wang, Y.-C., et al., "Coexistence and Post--Exercise Esacerbation of Intra-Left Ventricular Contractile Dyssynchrony in Medically Controlled Hypertensive Patients With Diastolic Dysfunction: A Tissue Doppler Echocardiography Study", Journal of American College of Cardiology, (Abstract No. 925-40, American College of Cardiology—55th Annual Scientific Sessions (ACC 2006)), (Feb. 21, 2006), p. 103A.

Zile, M. R., et al., "Right ventricular pacing reduces the rate of left ventricular relaxation and filling", J Am Coll Cardiol., 10(3), (Sep. 1987), 702-9.

* cited by examiner

PRE-EXCITATION PACING FOR TREATMENT OF HYPERTENSION

CLAIM OF PRIORITY

This application is a division of and claims benefit of priority under 35 U.S.C. §120 to U.S. patent application Ser. No. 11/557,202, filed on Nov. 7, 2006, now U.S. Pat. No. 8,046,070 and hereby incorporated by reference herein in its entirety.

FIELD OF THE INVENTION

This invention pertains to cardiac rhythm management devices such as pacemakers and other implantable devices.

BACKGROUND

Hypertension is abnormally high blood pressure and is one of the most common diseases afflicting humans. If left untreated, hypertension leads to multiple organ damage and is associated with much morbidity and mortality worldwide. Hypertension is an important risk factor for coronary heart disease, stroke, congestive heart failure, end-stage renal disease, and peripheral vascular disease.

Hypertension is defined with respect to systolic and/or diastolic pressure and may be either essential or secondary. Essential hypertension is hypertension where there is no identifiable secondary cause. Approximately 95% of American adults with hypertension have essential hypertension, while secondary hypertension accounts for fewer than 5% of the cases. The pathogenesis of essential hypertension is complex, and the factors involved may vary from patient to patient. Such factors could include, for example, abnormalities in blood vessel elasticity or resistance, cardiac output, circulating blood volume, and circulating hormone levels. Hypertension is most commonly treated by lifestyle modifications (e.g., diet and exercise) and various pharmacological agents. These treatments are not always effective in certain patients, however, and blood pressure medications are not without significant side effects.

DETAILED DESCRIPTION

When arterial blood pressure becomes elevated, the mechanical load that the heart must pump against, termed the afterload, is increased. The compensatory response of the heart to the increased afterload is hypertrophy, allowing the heart to pump more strongly against the elevated pressure. Although the hypertrophy may at first allow cardiac output to remain normal, it eventually causes various aberrations in ventricular function that lessen cardiac output and can progress to congestive heart failure. Left ventricular hypertrophy due to long-standing hypertension most commonly leads to diastolic dysfunction where the hypertrophic left ventricle is poorly compliant and does not relax normally during diastole, thus causing lessened diastolic filling and stroke volume. Studies have shown that patients with both hypertension and diastolic filling abnormalities exhibit an abnormal distribution of cardiac wall strain and stress. In most of these patients, the interventricular septum is both hypertrophic and mechanically delayed during contraction, causing it to contribute inordinately to the overall contraction. In other patients, a region of hypertrophy elsewhere may be mechanically delayed and similarly cause an abnormal strain/stress distribution in the ventricular wall. The abnormal contraction pattern of the ventricle produced by the regional hypertrophy causes a pressure waveform during systole that is more sharply peaked than normal. The result is in an increased peak pulse pressure and/or mean systolic blood pressure. Similar contraction patterns may also occur in patients who are hypertensive but not yet in diastolic heart failure.

Described herein are methods and apparatus for treating hypertension with electrical pre-excitation pacing therapy. As explained below, electrical pre-excitation of a hypertrophic region advances the timing of the regional contraction and reduces its contribution to the overall contraction. This may cause both an increase in stroke volume and a concomitant drop in systolic blood pressure. Such pre-excitation pacing therapy may be beneficial to hypertensive patients with an abnormal distribution of ventricular wall stress/strain, whether or nor they also have overt diastolic heart failure. Patients with hypertension who are not in heart failure often have similar underlying strain abnormalities that lead to the hypertrophy and diastolic filling abnormalities present in the patients with symptomatic heart failure. By treating these abnormalities early, it may be possible to halt or at least slow the progression to heart failure.

Pre-excitation pacing may be delivered by an implantable device that delivers electrical stimulation, for example, to the left ventricular septum (or other hypertrophic region) by an electrode positioned either in a coronary vein or elsewhere adjacent the ventricular septum. The device may incorporate multiple pacing electrodes from which one or more may be selected to fit different strain distributions. The timing of the stimulation with respect to atrial activation may be adjusted to reduce blood pressure while increasing or maintaining stroke volume. In one embodiment, the amount and/or timing of the stimulation may be controlled in a closed-loop fashion by means of a blood pressure and/or cardiac output sensor.

Pre-Excitation Pacing

The degree of tension on a muscle fiber before it contracts is termed the preload, while the degree of tension on a muscle fiber as it contracts is termed the afterload. Increasing the preload stretches a muscle fiber and also increases its maximum tension and velocity of shortening during contraction. With respect to the heart, the preload of a particular myocardial region is the myocardial wall stress at the end of diastole due to end-diastolic pressure and the forces applied by adjacent regions. The afterload of a myocardial region is the myocardial wall stress during systole due to the pressure load that the heart must pump against. When a myocardial region contracts late relative to other regions, the contraction of those other regions stretches the later contracting region and increases its preloading, thus causing an increase in the contractile force generated by the region. Conversely, a myocardial region that contracts earlier relative to other regions experiences decreased preloading and generates less contractile force. Because pressure within the ventricles rises rapidly from a diastolic to a systolic value as blood is pumped out into the aorta and pulmonary arteries, the parts of the ventricles that contract earlier during systole do so against a lower afterload than do parts of the ventricles contracting later. Thus, if a hypertrophic ventricular region responsible for an abnormally high pulse pressure can be made to contract earlier than other parts of the ventricle, it will be subjected to both a decreased preload and afterload. The region will then contract with less velocity and force during systole to result in decreased pulse pressure.

In order to cause early contraction and lessened stress, electro-stimulatory pacing pulses may be delivered to one or more sites in or around a hypertrophic region in a manner that pre-excites those sites relative to the rest of the ventricle. (As the term is used herein, a pacing pulse is any electrical stimulation of the heart of sufficient energy to initiate a propagating depolarization, whether or not intended to enforce a particular heart rate.) In a normal heartbeat, the specialized His-Purkinje conduction network of the heart rapidly conducts excitatory impulses from the sino-atrial node to the atrio-ventricular node, and thence to the ventricular myocardium to result in a coordinated contraction of both ventricles. Artificial pacing with an electrode fixed into an area of the myocardium does not take advantage of the heart's normal specialized conduction system for conducting excitation throughout the ventricles because the specialized conduction system can only be entered by impulses emanating from the atrio-ventricular node. Thus the spread of excitation from a ventricular pacing site must proceed only via the much slower conducting ventricular muscle fibers, resulting in the part of the ventricular myocardium stimulated by the pacing electrode contracting well before parts of the ventricle located more distally to the electrode.

Pre-excitation of a paced site relative to other sites can be used to deliberately change the distribution of wall stress experienced by the ventricle during the cardiac pumping cycle. Pacing therapy to unload a hypertrophic ventricular region may be implemented by pacing the ventricles at a single site in proximity to the hypertrophic region or by pacing at multiple ventricular sites in such proximity. In the latter case, the pacing pulses may be delivered to the multiple sites simultaneously or in a defined pulse output sequence. The single-site or multiple site pacing may be performed in accordance with a bradycardia pacing algorithm such as an inhibited demand mode or a triggered mode.

Exemplary Implantable Device

Figure 1:
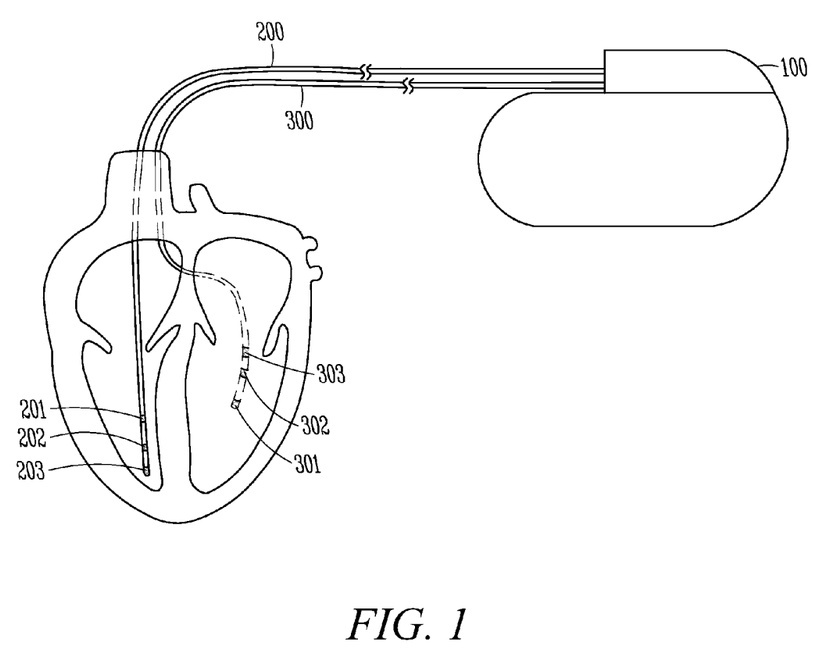
FIG. 1 illustrates the physical configuration of an exemplary pacing device.

FIG. 1 shows an implantable cardiac device 100 for delivering pre-excitation pacing therapy to a hypertrophic region as well as possibly other types of pacing therapy. Implantable pacing devices (also referred to herein as pacemakers, regardless of other functions that such devices may perform) are typically placed subcutaneously or submuscularly in a patient's chest with leads threaded intravenously into the heart to connect the device to electrodes disposed within a heart chamber that are used for sensing and/or pacing of the chamber. Electrodes may also be positioned on the epicardium by various means. A programmable electronic controller causes the pacing pulses to be output in response to lapsed time intervals and/or sensed electrical activity (i.e., intrinsic heart beats not as a result of a pacing pulse). The device senses intrinsic cardiac electrical activity through one or more sensing channels, each of which incorporates one or more of the electrodes. In order to excite myocardial tissue in the absence of an intrinsic beat, pacing pulses with energy above a certain threshold are delivered to one or more pacing sites through one or more pacing channels, each of which incorporates one or more of the electrodes. FIG. 1 shows the exemplary device having two leads 200 and 300, each of which is a multi-polar (i.e., multi-electrode) lead having electrodes 201-203 and 301-303, respectively. The electrodes 201-203 are disposed in the right ventricle in order to excite or sense right ventricular or septal regions, while the electrodes 301-303 are disposed in the coronary sinus or cardiac veins in order to excite or sense regions of the left ventricle. Other embodiments may use any number of electrodes in the form of unipolar and/or multi-polar leads in order to excite different myocardial sites. As explained below, once the device and leads are implanted, the pacing and/or sensing channels of the device may be configured with selected ones of the multiple electrodes in order to selectively pace or sense a particular myocardial site(s).

Figure 2:
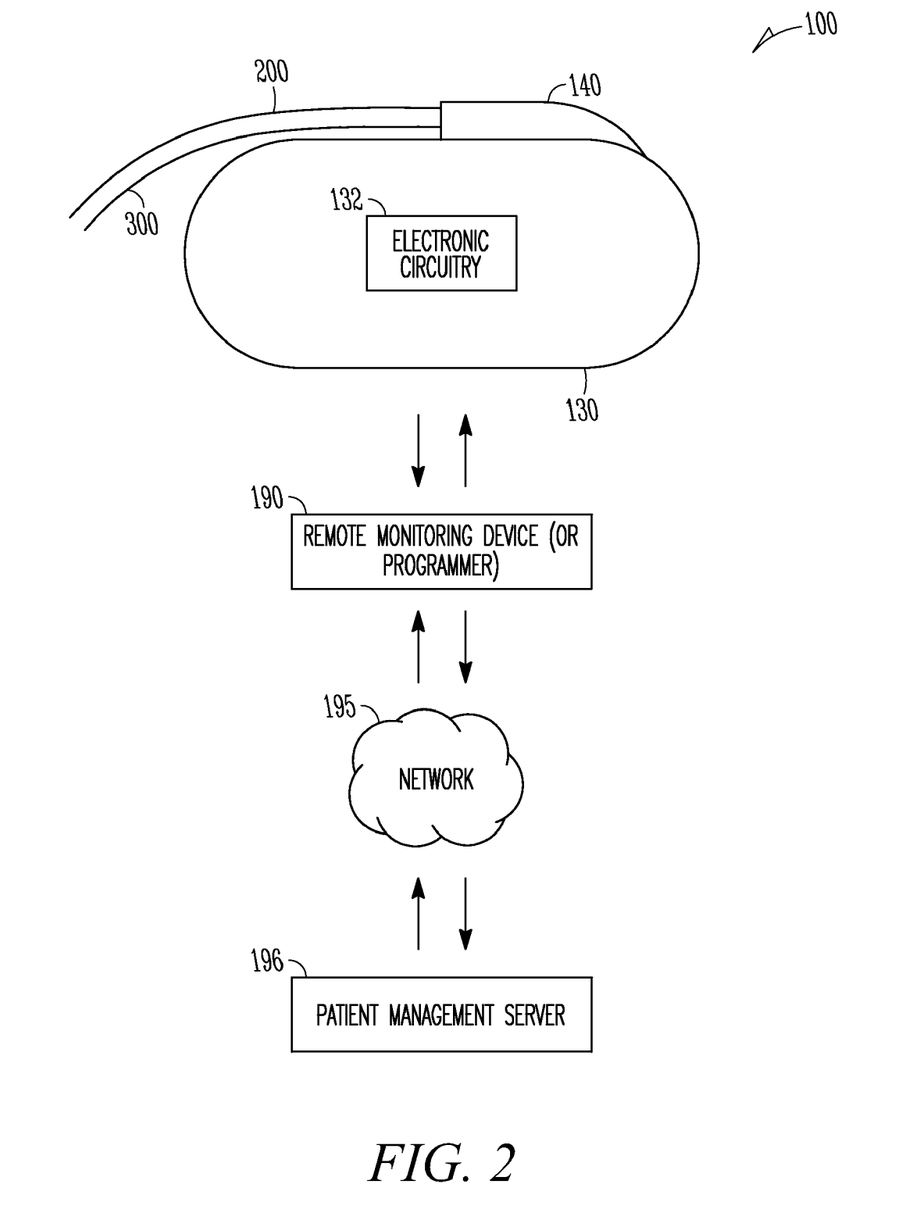
FIG. 2 shows the components of an exemplary device.

FIG. 2 shows the components of the implantable device 100 in more detail as well as an exemplary monitoring/programming system. The implantable device 100 includes a hermetically sealed housing 130 that is placed subcutaneously or submuscularly in a patient's chest. The housing 130 may be formed from a conductive metal, such as titanium, and may serve as an electrode for delivering electrical stimulation or sensing in a unipolar configuration. A header 140, which may be formed of an insulating material, is mounted on the housing 130 for receiving leads 200 and 300 which may be then electrically connected to pulse generation circuitry and/or sensing circuitry. Contained within the housing 130 is the electronic circuitry 132 for providing the functionality to the device as described herein which may include a power supply, sensing circuitry, pulse generation circuitry, a programmable electronic controller for controlling the operation of the device, and a telemetry transceiver capable of communicating with an external programmer or a remote monitoring device 190. An external programmer wirelessly communicates with the device 100 and enables a clinician to receive data and modify the programming of the controller. A remote monitoring device also communicates via telemetry with the device 100 and may be further interfaced to a network 195 (e.g., an internet connection) for communicating with a patient management server 196 that allows clinical personnel at remote locations to receive data from the remote monitoring device as well as issue commands. The controller may be programmed such when particular conditions are detected by the monitoring circuitry (such as when a measured parameter exceeds or falls below a specified limit value), the device transmits an alarm message to the remote monitoring device and to the patient management server to alert clinical personnel.

Figure 3:
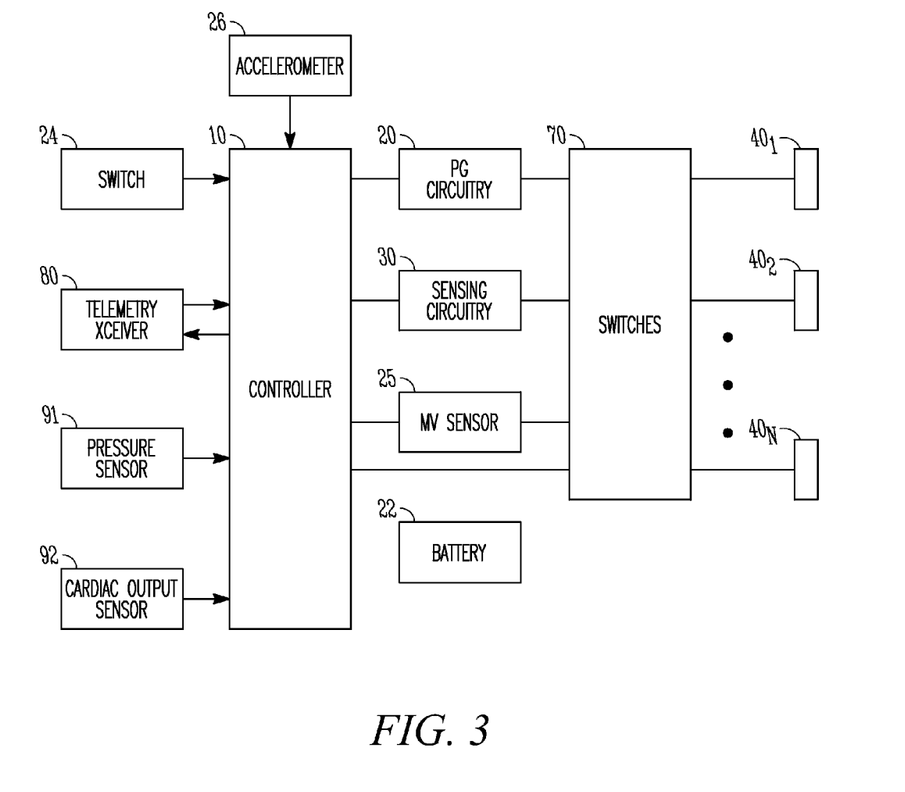
FIG. 3 is a block diagram of the electronic circuitry of an exemplary device.

A block diagram of the circuitry 132 is illustrated in FIG. 3. A battery 22 supplies power to the circuitry. The controller 10 controls the overall operation of the device in accordance with programmed instructions and/or circuit configurations. The controller may be implemented as a microprocessor-based controller and include a microprocessor and memory for data and program storage, implemented with dedicated hardware components such as ASICs (e.g., finite state machines), or implemented as a combination thereof. The controller also includes timing circuitry such as external clocks for implementing timers used to measure lapsed intervals and schedule events. As the term is used herein, the programming of the controller refers to either code executed by a microprocessor or to specific configurations of hardware components for performing particular functions. Interfaced to the controller are sensing circuitry 30 and pulse generation circuitry 20 by which the controller interprets sensing signals and controls the delivery of paces in accordance with a pacing mode. The sensing circuitry 30 receives atrial and/or ventricular electrogram signals from sensing electrodes and includes sensing amplifiers, analog-to-digital converters for digitizing sensing signal inputs from the sensing amplifiers, and registers that can be written to for adjusting the gain and threshold values of the sensing amplifiers. The pulse generation circuitry 20 delivers pacing pulses to pacing electrodes disposed in the heart and includes capacitive discharge pulse generators, registers for controlling the pulse generators, and registers for adjusting pacing parameters such as pulse energy (e.g., pulse amplitude and width). The device allows adjustment of the pacing pulse energy in order to ensure capture of myocardial tissue (i.e., initiating of a propagating action potential) by a pacing pulse. The pulse generation circuitry may also include a shocking pulse generator for delivering a defibrillation/cardioversion shock via a shock electrode upon detection of a tachyarrhythmia. A telemetry transceiver 80 is interfaced to the controller which enables the controller to communicate with an external programmer and/or a remote monitoring unit. The telemetry transceiver may also be used to wirelessly connect the implantable device to an external sensor such as for measuring blood pressure. A magnetically or tactilely actuated switch 24 is also shown as interfaced to the controller to allow the patient to signal certain conditions or events to the implantable device.

A pacing channel is made up of a pulse generator connected to an electrode, while a sensing channel is made up of a sense amplifier connected to an electrode. Shown in the figure are electrodes $40_1$ through $40_N$ where N is some integer. The electrodes may be on the same or different leads and are electrically connected to a MOS switch matrix 70. The switch matrix 70 is controlled by the controller and is used to switch selected electrodes to the input of a sense amplifier or to the output of a pulse generator in order to configure a sensing or pacing channel, respectively. The device may be equipped with any number of pulse generators, amplifiers, and electrodes that may be combined arbitrarily to form sensing or pacing channels. The switch matrix 70 allows selected ones of the available implanted electrodes to be incorporated into sensing and/or pacing channels in either unipolar or bipolar configurations. A bipolar sensing or pacing configuration refers to the sensing of a potential or output of a pacing pulse between two closely spaced electrodes, where the two electrodes are usually on the same lead (e.g., a ring and tip electrode of a bipolar lead or two selected electrodes of a multi-polar lead). A unipolar sensing or pacing configuration is where the potential sensed or the pacing pulse output by an electrode is referenced to the conductive device housing or another distant electrode.

The device illustrated in FIG. 3 may be configured with multiple sensing and/or pacing channels that may be either atrial or ventricular channels depending upon the location of the electrode. The device is therefore capable of delivering single-site or multiple site ventricular pre-excitation pacing for purposes of treating hypertension as well as conventional pacing. The switch matrix allows particular myocardial sites to be pre-excited by selecting the appropriately disposed electrode(s) to be incorporated into a pacing channel used to deliver pre-excitation pacing. Configuration of pacing and sensing channels may be performed via an external programmer communicating through the telemetry interface or, as discussed below, may be performed automatically by the controller executing a configuration algorithm.

Pre-excitation pacing may be delivered as single-site pacing, biventricular pacing where one of the ventricles is pre-excited relative to the other as determined by a programmed biventricular offset interval, or delivered as multi-site ventricular pacing. In the case where the pre-excitation pacing is delivered at multiple sites, the sites may be paced simultaneously or in accordance with a particular pulse output sequence that specifies the order and timing in which the sites are to be paced during a single beat. When an electrogram signal in an atrial or ventricular sensing channel exceeds a specified threshold, the controller detects an atrial or ventricular sense, respectively, which pacing algorithms may employ to trigger or inhibit pacing. The controller is capable of operating the device in a number of programmed modes where a programmed mode defines how pacing pulses are output in response to sensed events and expiration of time intervals. Pre-excitation pacing of one or more ventricular sites may be delivered in conjunction with a bradycardia pacing mode, which refers to a pacing algorithm that enforces a certain minimum heart rate, and may include or not include pacing pulses delivered to the atria or ventricles for other purposes (e.g., treatment of bradycardia) Inhibited demand bradycardia pacing modes utilize escape intervals to control pacing in accordance with sensed intrinsic activity. In an inhibited demand ventricular pacing mode, the ventricle is paced during a cardiac cycle only after expiration of a defined escape interval during which no intrinsic beat by the chamber is detected. For example, a ventricular escape interval can be defined between ventricular events so as to be restarted with each ventricular sense or pace, referred to as lower rate interval (LRI). The inverse of this escape interval is the minimum rate at which the pacemaker will allow the ventricles to beat, sometimes referred to as the lower rate limit (LRL). Paces may also be delivered in a rate-adaptive pacing mode where the lower rate interval and/or other escape intervals are modified in accordance with a measured exertion level such as with accelerometer 26 or minute ventilation sensor 25. In atrial tracking and AV sequential pacing modes, another ventricular escape interval is defined between atrial and ventricular events, referred to as the atrio-ventricular interval (AVI) or AV delay interval. The atrio-ventricular interval is triggered by an atrial sense or pace and stopped by a ventricular sense or pace. A ventricular pace is delivered upon expiration of the atrio-ventricular interval if no ventricular sense occurs before the expiration. Multi-site pacing modes may use other pacing parameters that specify the timing of pacing pulses such as a VV delay interval that specifies the timing between paces delivered to both ventricles or different sites in the same ventricle.

Also shown in FIG. 3 as communicating with the controller are a pressure sensor 91 and a cardiac output sensor 92. As explained below, in one embodiment, either or both of these sensors may be used for automatic configuration of pre-excitation pacing channels, closed-loop control of the amount of pre-excitation pacing, and/or closed-loop control of timing parameters. Either or both of the sensors may be incorporated into leads that are intravascularly disposed or may be external devices that communicate with the controller wirelessly via telemetry. The pressure sensor 91 and cardiac output sensor 92 generate signals that are related to a patient's blood pressure and cardiac output, respectively, and may be any type of transducers for those purposes. The cardiac output sensor 92, for example, could be a flow sensor or an impedance sensor for measuring cardiac volumes such as end-diastolic filling volume.

Delivery of Anti-Hypertension Pre-Excitation Pacing

As described above, some hypertensive patients exhibit abnormal stress/strain distributions in the left ventricle during systole due to a late-contracting, hypertrophied region of the ventricle. The hypertrophied region in these patients may thus contribute inordinately to the contraction and cause an abnormal systolic pressure waveform. Such an abnormal systolic pressure may cause or contribute to the patient's hypertension. By pre-excitation of the hypertrophied region or regions with pacing pulses, the region may be made to contract earlier during systole in order to at least partially normalize the stress/strain distribution and resulting systolic pressure waveform, thereby reducing the patient's hypertension. The more normal systolic pressure waveform may also result in an improved cardiac output.

Hypertensive patients most likely to benefit from pre-excitation pacing therapy may be identified, for example, with clinical studies that demonstrate an abnormal left ventricular systolic pressure waveform, abnormal contraction pattern, and/or region(s) of hypertrophy. A pacemaker is then implanted with one or more pacing electrodes disposed near the hypertrophied region so as to provide the desired pre-excitation. The pacemaker may be programmed to deliver the ventricular pre-excitation pacing in accordance with a bradycardia pacing mode such as an atrial tracking or AV sequential mode. Variables such as cardiac output and/or blood pressure may also be measured and taken into account in order to optimally select pre-excitation pacing sites and/or pacing parameter values (e.g., AV and VV delay intervals). For example, the AV delay interval may be adjusted for atrial tracking or AV sequential modes to a value that optimizes ventricular filling and resulting cardiac output. Different pre-excitation pacing sites may be tested, either by changing lead implant sites or by reconfiguring pacing channels after implantation, while the patient's blood pressure is measured in order to determine the site(s) for delivering pre-excitation pacing that optimally reduces systolic blood pressure. The patient may also be challenged with a drug that raises blood pressure while testing different pacing sites and/or pacing parameter values for efficacy in lowering blood pressure. As described below, a pacemaker may also be configured to automatically determine pre-excitation pacing sites and/or pacing parameters based upon sensor measurement.

As noted, some patients may experience an improvement in cardiac output from pre-excitation due to normalization of the systolic pressure waveform. In these patients, the pacemaker may be programmed to deliver pre-excitation pacing on a continuous basis similar to the way most pacemaker patients are treated for bradycardia. In other patients, cardiac output may be lessened somewhat as systolic pressure is reduced by the pre-excitation pacing. In this group of patients, it may be desirable for the pre-excitation pacing to be delivered intermittently. The pacemaker could then be programmed to deliver pre-excitation pacing in accordance with a programmed pre-excitation pacing mode only when the device is operating in a pre-excitation state, where the pre-excitation state is duty cycled. The pacemaker could then duty cycle the pre-excitation state in accordance with a schedule based upon lapsed time intervals and/or in accordance with sensed events or conditions. For example, the pre-excitation state may be entered only at certain times of the day (e.g., at night) and for specified durations. In another example, the pacemaker is equipped with an exertion level sensor (e.g., an accelerometer for measuring activity or a minute ventilation sensor for measuring respiration) and be programmed to enter or exit the pre-excitation state if the patient's measured exertion level within some specified range. In a chronotropically competent patient, heart rate may be used in a similar manner as exertion level to control entering or exiting the pre-excitation state. As described below, the pacemaker could also be configured with the capability of measuring blood pressure and/or cardiac output to enable closed-loop duty cycling of the pre-excitation state based upon those variables.

Closed-Loop Control of Anti-Hypertension Pre-Excitation Pacing

As shown in FIG. 3, an implantable pacing device for delivering pre-excitation pacing to treat hypertension may be equipped with sensors for measuring variables related to blood pressure and/or cardiac output. The blood pressure and/or cardiac output measurements thereby obtained may be instantaneous measurements or may be averages taken over some specified period of time. As described below, the device may be programmed to control anti-hypertension pre-excitation pacing in a closed-loop manner by varying the duty cycle of the pre-excitation state, varying pre-excitation pacing parameters such as the AV delay interval or pacing mode, and/or automatically configuring pre-excitation pacing channels in accordance with such blood pressure and/or cardiac output measurements.

In an exemplary embodiment, an implantable pacing device is configured with one or more pre-excitation pacing channels that include pulse generating circuitry and one or more electrodes adapted for disposition near one or more myocardial sites. The device controller is programmed to deliver paces through the pre-excitation pacing channel(s) in accordance with a programmed pre-excitation pacing mode when the device is operating in a pre-excitation state. For example, the controller can be programmed to deliver pre-excitation pacing as ventricular pacing in accordance with an atrial tracking or AV sequential pacing mode such that one or more pre-excitation paces are delivered upon expiration of a programmed AV delay interval following an atrial sense When the device is in a non-pre-excitation state, it may deliver no pacing therapy at all or may deliver pacing therapy for another purpose (e.g., bradycardia pacing) using a pacing site or mode other than that used for pre-excitation pacing. The device further includes a blood pressure sensor communicating with the controller for generating a signal related to a patient's arterial blood pressure, the controller being programmed to derive a blood pressure measurement therefrom. The blood pressure measurement may be derived instantaneously from the blood pressure signal or be derived from an average of the blood pressure signal pressure as generated over a specified period of time. The controller is then programmed to duty cycle the pre-excitation state such that the amount of pre-excitation pacing delivered by the device is increased if the blood pressure measurement increases to a specified extent. The device may also incorporate a cardiac output sensor for measuring a variable related to a patient's cardiac output. The controller can then be programmed to adjust the AV delay interval used during pre-excitation pacing in a manner that maximizes the value of the cardiac output measurement.

Figure 4:
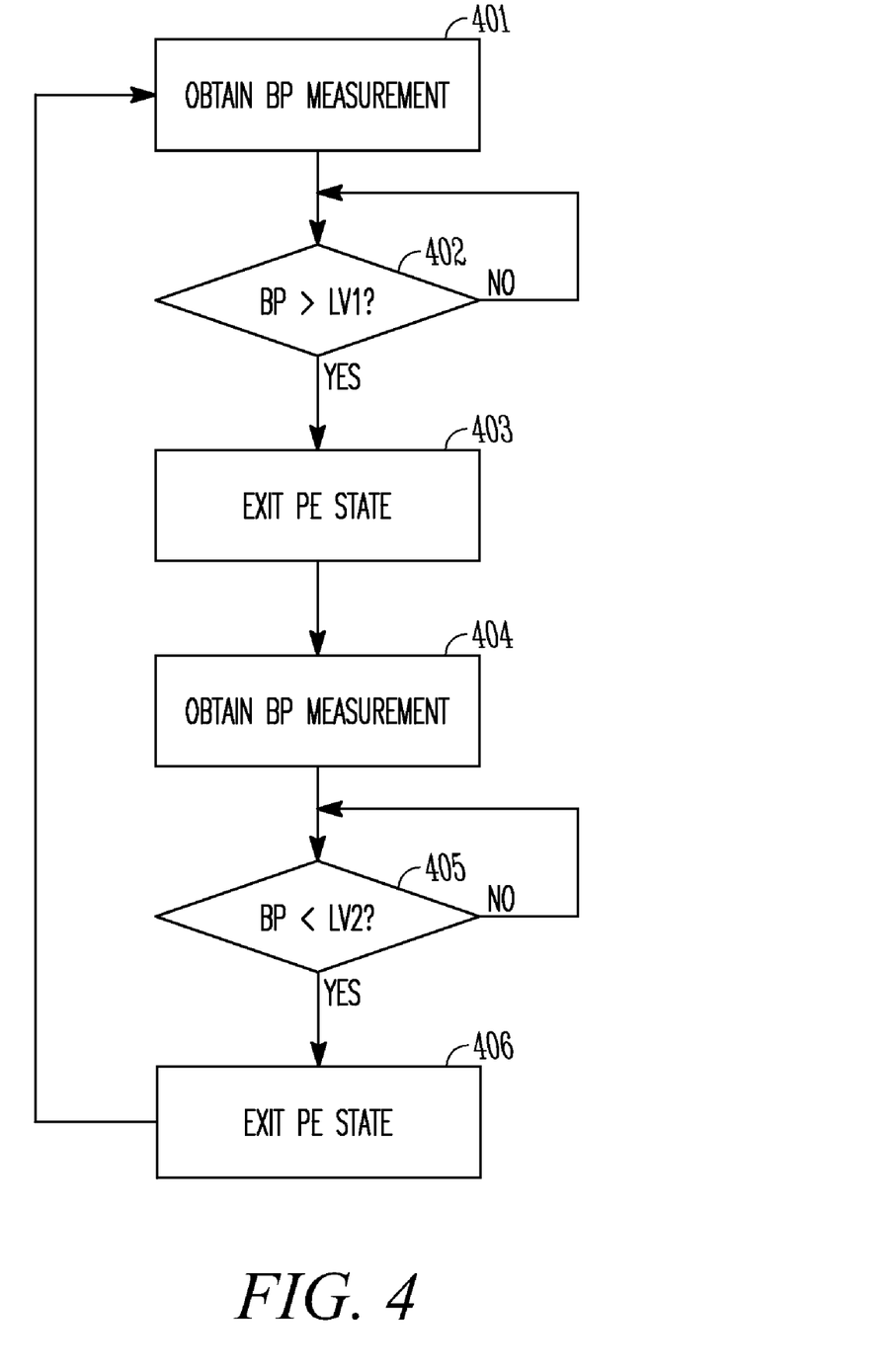
FIG. 4 illustrates an exemplary algorithm for duty cycling the pre-excitation state.

In one embodiment, the controller is programmed to duty cycle the pre-excitation state by entering the pre-excitation state if the blood pressure measurement is above a first limit value and exiting the pre-excitation state if the blood pressure measurement is below a second limit value, where the first and second limit values may be the same or different. FIG. 4 illustrates an exemplary algorithm that could be executed by the controller to implement such duty cycling. The algorithm begins after the device has exited the pre-excitation (PE) state and is in a non-pre-excitation state where no pre-excitation pacing is being delivered. At step 401, the device obtains a blood pressure measurement BP. At step 402, the blood pressure measurement is compared with a first limit value LV1. The device continues to monitor blood pressure while in the non-PE state. When the blood pressure measurement rises above the first limit value, the device enters the PE state at step 403 and delivers pre-excitation pacing. At step 404, a blood pressure measurement is again obtained. At step 405, the blood pressure measurement is compared with a second limit value LV2. The device continues to monitor blood pressure while delivering pre-excitation pacing in the PE state. When the blood pressure measurement falls below the second limit value, the PE state is exited at step 406, and the device returns to step 401.

Figure 5:
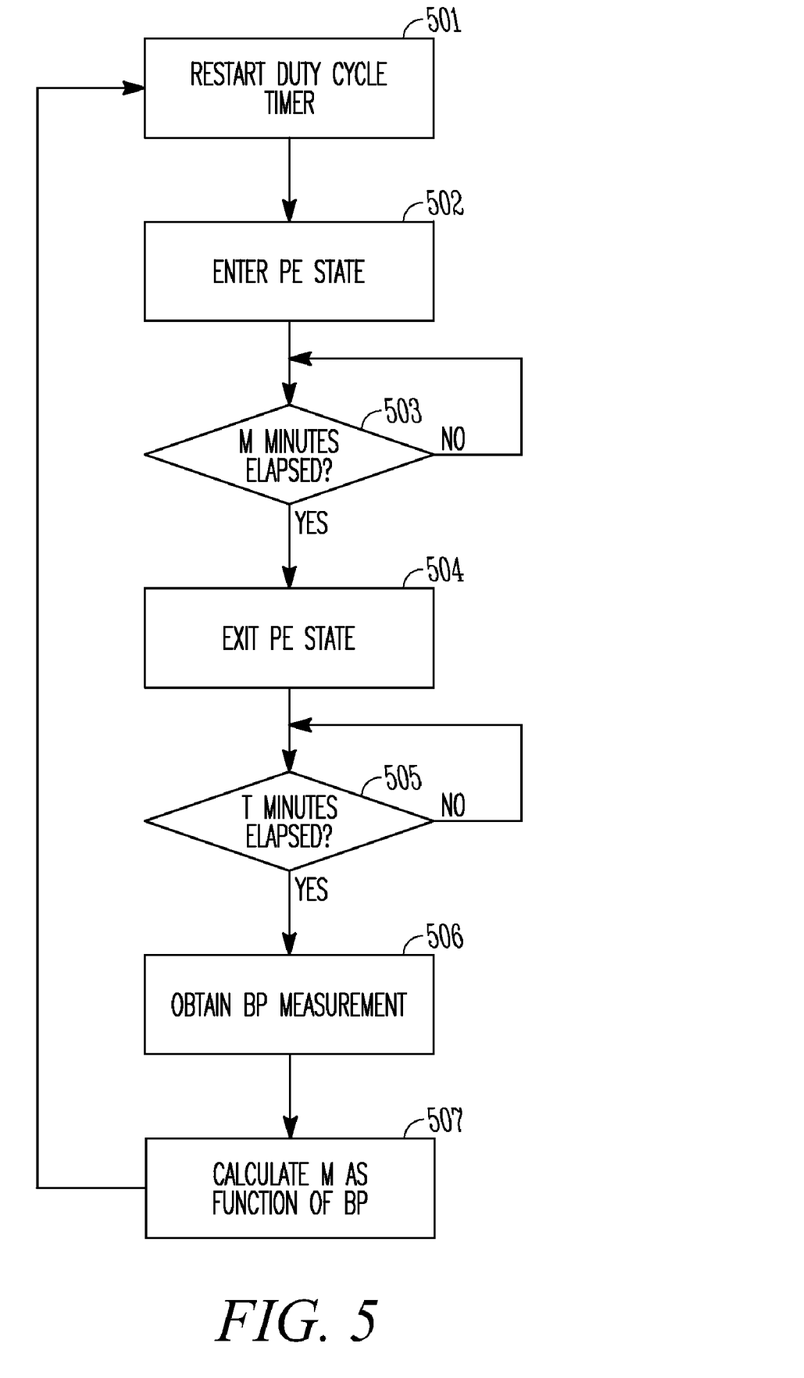
FIG. 5 illustrates another exemplary algorithm for duty cycling the pre-excitation state.

In another embodiment, the controller is programmed to duty cycle the pre-excitation state by entering and exiting the pre-excitation state in accordance with a schedule based upon lapsed time intervals and further programmed to modify the schedule to increase the duration of the pre-excitation state if the blood pressure measurement increases to some specified extent. FIG. 5 illustrates an exemplary algorithm that could be executed by the controller to implement such duty cycling. The algorithm begins after the device has exited the pre-excitation (PE) state and is in a non-pre-excitation state where no pre-excitation pacing is being delivered. At step 501, a duty cycle timer is started which counts from zero to T minutes (or other unit of time) where T is some specified value. At step 502, the device enters the PE state and begins delivering pre-excitation pacing. At step 503, while continuing to operate in the PE state, the device monitors the duty cycle timer until M minutes have elapsed, at which point the device exits the PE state at step 504. The device monitors the duty cycle timer at step 505 until T minutes have elapsed and then obtains a blood pressure measurement BP at step 506. The value of M (i.e., the number of minutes for which the device operates in the pre-excitation state out of every T minutes) is then calculated as a function of the blood pressure measurement BP at step 507. The function for mapping the blood pressure measurement to a value for M could be simple, such as where the value of M alternates between two values according to the value of the blood pressure measurement, or more complicated. In the latter instance, the function could be implemented as a look-up table.

The device may also be configured to use one or more entry and/or exit conditions in controlling entry and/or exit into the PE state. An entry or exit condition could be, for example, specified time(s) of the day, actuation of a switch by the patient (e.g., a magnetically or tactilely actuated switch interfaced to the device controller), a command received via telemetry, or a measured variable being within or out of a specified range. Examples of such measured variables include heart rate, activity level, minute ventilation, cardiac output, and blood pressure. A plurality of entry and/or exit conditions may also be logically ORed or ANDed together to determine whether a composite entry or entry condition is satisfied. In some embodiments, the device may be programmed to simply enter and/or exit the PE state in accordance with one or more specified entry or exit conditions. In other embodiments, one or more specified entry and/or exit conditions are used to permit and/or prohibit, respectively, duty cycling of the PE state such as described above with reference to FIGS. 4 and 5 or other duty cycling schemes based upon lapsed time intervals and/or a sensed variables such as blood pressure and cardiac output.

The device may also incorporate a switching matrix operable by the controller for configuring pacing channels with selected pacing electrodes. The controller may be programmed to periodically reconfigure the pre-excitation pacing channel(s) with a different selected pacing electrode in order prevent hypertrophy from developing at a region excited later during systole as a result of pre-excitation pacing. For example, the device could periodically switch between right ventricular pacing and left ventricular pacing. The controller could also be programmed to optimally configure the pre-excitation pacing channel(s) by sequentially reconfiguring the pre-excitation pacing channel(s) with different pacing electrodes and selecting the pacing electrode for use in the pre-excitation pacing channel(s) that results in the greatest decrease in the blood pressure measurement. The controller may be further programmed to sequentially test different pacing modes (e.g., right ventricular, left ventricular, biventricular, or multi-site ventricular pacing) and/or pacing parameters (e.g., AV delay interval, VV delay interval) and to select the pacing mode and/or parameter for use in the pre-excitation state that results in the greatest decrease in the blood pressure measurement. A cardiac output measurement could be combined with the blood pressure measurement in configuring pacing channels, selecting pacing modes, and/or adjusting pacing parameters in order to optimize both blood pressure reduction and cardiac output improvement.

The invention has been described in conjunction with the foregoing specific embodiments. It should be appreciated that those embodiments may also be combined in any manner considered to be advantageous. Also, many alternatives, variations, and modifications will be apparent to those of ordinary skill in the art. Other such alternatives, variations, and modifications are intended to fall within the scope of the following appended claims.

What is claimed is:

1. A method, comprising:
   identifying a patient as having hypertension;
   implanting a pacemaker in the patient;
   measuring the patient's blood pressure;
   selecting a pacing mode, one or more pacing sites, and pacing parameter values to deliver pre-excitation pacing that optimally decrease the patient's blood pressure.

2. The method of claim 1 further comprising measuring the patient's cardiac output and selecting a pacing mode, one or more pacing sites, and pacing parameter values that optimally decrease the patient's blood pressure while maintaining adequate cardiac output.

3. The method of claim 1 further comprising programming the pacemaker to deliver pre-excitation pacing intermittently according to a defined schedule.

4. The method of claim 1 further comprising programming the pacemaker to deliver pre-excitation pacing intermittently in accordance with whether a measured heart rate is within or outside of a specified range.

5. The method of claim 1 further comprising programming the pacemaker to deliver pre-excitation pacing intermittently in accordance with whether a measured activity level is within or outside of a specified range.

6. The method of claim 1 further comprising programming the pacemaker to deliver pre-excitation pacing intermittently in accordance with whether a measured activity level is within or outside of a specified range.

7. The method of claim 1 further comprising challenging the patient with a drug that raises blood pressure while testing different pacing sites and/or pacing parameter values for efficacy in lowering blood pressure.

8. The method of claim 1 further comprising providing the patient with a means for stopping or starting pre-excitation pacing.

9. The method of claim 1 further comprising optimally configuring a pacing channel of the pacemaker by sequentially reconfiguring the pacing channel with different pacing electrodes and selecting the pacing electrode for use in the pacing channel that results in the greatest decrease in the blood pressure measurement during delivery of pre-excitation pacing.

10. A method for operating a pacing device, comprising:
    delivering paces through one or more pre-excitation pacing channel(s) in accordance with a programmed pre-excitation pacing mode when the device is operating in a pre-excitation state;

generating a signal related to a patient's arterial blood pressure and deriving a blood pressure measurement therefrom;

duty cycling the pre-excitation state such that the amount of pre-excitation pacing delivered by the device is increased if the blood pressure measurement increases to a specified extent.

11. The method of claim 10 further comprising duty cycling the pre-excitation mode by entering the pre-excitation mode if the blood pressure measurement is above a first limit value and exiting the pre-excitation mode if the blood pressure measurement is below a second limit value.

12. The method of claim 10 further comprising duty cycling the pre-excitation mode by entering and exiting the pre-excitation mode in accordance with a schedule based upon lapsed time intervals and wherein the controller is further programmed to modify the schedule to increase the duration of the pre-excitation mode if the blood pressure measurement increases to the specified extent.

13. The method of claim 10 wherein the blood pressure measurement is an average of the signal related to a patient's arterial blood pressure as generated over a specified period of time.

14. The method of claim 10 further comprising measuring a variable related to a patient's exertion level and exiting the pre-excitation mode if the exertion level measurement increases above a specified threshold value.

15. The method of claim 14 wherein the measured variable is minute ventilation.

16. The method of claim 10 further comprising:
measuring a variable related to a patient's cardiac output;
delivering pre-excitation pacing as ventricular pacing in accordance with an atrial tracking or AV sequential pacing algorithm such that one or more pre-excitation paces are delivered upon expiration of a programmed AV delay interval following an atrial sense or pace; and,
adjusting the AV delay interval during pre-excitation pacing in a manner that maximizes the value of the cardiac output measurement.

17. The method of claim 10 further comprising periodically reconfiguring the pre-excitation pacing channel(s) with a different pacing electrode.

18. The method of claim 10 further comprising optimally configuring the pre-excitation pacing channel(s) by sequentially reconfiguring the pre-excitation pacing channel(s) with different pacing electrodes and selecting the pacing electrode for use in the pre-excitation pacing channel(s) that results in the greatest decrease in the blood pressure measurement.

19. The method of claim 10 further comprising sequentially testing different pacing configurations and selecting the pacing configuration for use in the pre-excitation mode that results in the greatest decrease in the blood pressure measurement.

20. The method of claim 10 further comprising sequentially testing different values of one or more pacing parameters and selecting the values of the one or more pacing parameters for use in the pre-excitation mode that result in the greatest decrease in the blood pressure measurement.

* * * * *